United States Patent
Shanley

(10) Patent No.: US 6,855,125 B2
(45) Date of Patent: Feb. 15, 2005

(54) EXPANDABLE MEDICAL DEVICE DELIVERY SYSTEM AND METHOD

(75) Inventor: John F. Shanley, Redwood City, CA (US)

(73) Assignee: Conor Medsystems, Inc., Menlo Park, CA (US)

( * ) Notice: Subject to any disclaimer, the term of this patent is extended or adjusted under 35 U.S.C. 154(b) by 373 days.

(21) Appl. No.: 09/867,382

(22) Filed: May 31, 2001

(65) Prior Publication Data

US 2001/0027291 A1 Oct. 4, 2001

Related U.S. Application Data

(62) Division of application No. 09/315,885, filed on May 20, 1999, now Pat. No. 6,290,673.

(51) Int. Cl.⁷ .............................................. A61M 29/00
(52) U.S. Cl. .................................................. 604/102.02
(58) Field of Search ........................ 604/96.01, 101.01; 606/192–194, 101.02–101.5, 102.01–102.03, 915, 916, 917, 918, 919, 920, 921, 93.01, 164.01, 164.02–164.09, 103.01–103.14, 191

(56) References Cited

U.S. PATENT DOCUMENTS

| | | |
|---|---|---|
| 3,657,744 A | 4/1972 | Ersek |
| 4,300,244 A | 11/1981 | Bukros |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wollnsky |
| 4,834,755 A | 5/1989 | Silvestrini et al. |

(List continued on next page.)

FOREIGN PATENT DOCUMENTS

| | | |
|---|---|---|
| CA | 2234787 | 4/1998 |
| DE | 2002 00 220 | 3/2002 |

(List continued on next page.)

OTHER PUBLICATIONS

U.S. Appl. No. 09/932,093, filed Aug. 20, 2001, Shanley.
Emanelsson, H., et al., *The Jostent Coronary Stent Range*, Ch. 19.
Hwang, C–W, et al. "Physiological Transport forces Govern Drug distribution for Stent–based Delivery".

*Primary Examiner*—Manuel Mendez
(74) *Attorney, Agent, or Firm*—Cindy A. Lynch

(57) ABSTRACT

A delivery system and method are provided for accurately locating, orienting, and implanting expandable tissue supporting devices at a lumen junction or bifurcation in a body lumen. For example, the system may be used to deliver a tissue supporting device to a bifurcated artery such that, on expansion, the tissue supporting device provides side ports of a specific size and geometry to accommodate bifurcations in the artery. The delivery system is capable of accurately orienting these side ports both radially and longitudinally with respect to branch lumen openings of the artery. The delivery system achieves orientation by utilizing a guide member which is positioned to extend from the side port feature of the tissue supporting device. The guide member is tracked along a guidewire which extends into the branch lumen, ultimately orienting the side port of the tissue supporting device properly at the branch lumen opening. After expansion of the tissue supporting device, the guide member drops out of the enlarged side port and is withdrawn.

14 Claims, 9 Drawing Sheets

U.S. PATENT DOCUMENTS

| | | |
|---|---|---|
| 4,955,878 A | 9/1990 | See et al. |
| 4,957,508 A | 9/1990 | Kaneko et al. |
| 4,960,790 A | 10/1990 | Steela et al. |
| 4,969,458 A | 11/1990 | Wiktor |
| 4,989,601 A | 2/1991 | Marchosky et al. |
| 4,990,155 A | 2/1991 | Wilkoff |
| 4,994,071 A | 2/1991 | MacGregor |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya et al. |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,267,958 A * | 12/1993 | Buchbinder et al. ... 604/103.14 |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffman et al. |
| 5,338,300 A * | 8/1994 | Cox ...................... 604/103.05 |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narcisco, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrx |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,473,055 A | 12/1995 | Mongelli et al. |
| 5,499,373 A | 3/1996 | Richards et al. |
| 5,520,647 A * | 5/1996 | Solar ..................... 604/102.02 |
| 5,523,092 A | 6/1996 | Hanson et al. |
| 5,545,210 A | 8/1996 | Hess et al. |
| 5,549,556 A * | 8/1996 | Ndondo-Lay et al. ... 604/103.1 |
| 5,551,954 A | 9/1996 | Buscemi et al. |
| 5,556,413 A | 9/1996 | Lam |
| 5,575,771 A | 11/1996 | Walinsky |
| 5,578,075 A | 11/1996 | Dayton |
| 5,593,434 A | 1/1997 | Williams |
| 5,607,442 A | 3/1997 | Fischell et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,667,764 A | 9/1997 | Kopia et al. |
| 5,674,278 A | 10/1997 | Boneau |
| 5,697,971 A | 12/1997 | Fischell et al. |
| 5,707,385 A | 1/1998 | Williams |
| 5,713,949 A | 2/1998 | Jayaranman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,776,181 A | 7/1998 | Lee et al. |
| 5,800,507 A | 9/1998 | Schwartz |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,957,971 A | 9/1999 | Schwartz |
| 5,964,798 A | 10/1999 | Imran |
| 5,968,092 A | 10/1999 | Buxcemi et al. |
| 5,972,027 A | 10/1999 | Johnson |
| 5,976,182 A | 11/1999 | Cox |
| 5,984,957 A | 11/1999 | Laptewicz, Jr. et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,027,526 A | 2/2000 | Limon et al. |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,120,535 A | 9/2000 | McDonald et al. |
| 6,120,847 A | 9/2000 | Yang et al. |
| 6,153,252 A | 11/2000 | Hossainy et al. |
| 6,156,062 A | 12/2000 | McGuinness |
| 6,159,488 A | 12/2000 | Nagler et al. |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,210,429 B1 | 4/2001 | Vardi et al. |
| 6,221,090 B1 * | 4/2001 | Wilson ...................... 606/194 |

| | | |
|---|---|---|
| 6,231,600 B1 | 5/2001 | Zhong |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,273,908 B1 | 8/2001 | Ndondo-Lay |
| 6,273,910 B1 | 8/2001 | Limon |
| 6,273,911 B1 | 8/2001 | Cox et al. |
| 6,273,913 B1 | 8/2001 | Wright et al. |
| 6,280,411 B1 | 8/2001 | Lennox |
| 6,290,673 B1 * | 9/2001 | Shanley .................. 604/102.02 |
| 6,293,967 B1 | 9/2001 | Shanley |
| 6,309,414 B1 | 10/2001 | Rolando et al. |
| 6,312,460 B2 | 11/2001 | Drasler et al. |
| 6,395,326 B1 | 5/2002 | Castro et al. |
| 6,451,051 B2 | 9/2002 | Drasler et al. |
| 6,468,302 B2 | 10/2002 | Cox et al. |
| 6,475,237 B2 | 11/2002 | Drasler et al. |
| 6,506,411 B2 | 1/2003 | Hunter et al. |
| 6,506,437 B1 | 1/2003 | Harish et al. |
| 6,511,505 B2 | 1/2003 | Cox et al. |
| 6,540,774 B1 | 4/2003 | Cox |
| 6,544,544 B2 | 4/2003 | Hunter et al. |
| 6,558,733 B1 | 5/2003 | Hossainy et al. |
| 6,562,065 B1 | 5/2003 | Shanley |
| 6,565,602 B2 | 5/2003 | Rolando et al. |
| 6,602,284 B2 | 8/2003 | Cox et al. |
| 6,616,690 B2 | 9/2003 | Rolando et al. |
| 6,706,061 B1 | 3/2004 | Fischell et al. |
| 6,706,062 B2 | 3/2004 | Vardi et al. |
| 2001/0000802 A1 | 5/2001 | Soykan et al. |
| 2001/0027340 A1 | 10/2001 | Wright et al. |
| 2001/0034363 A1 | 10/2001 | Li et al. |
| 2001/0044648 A1 | 11/2001 | Wolinsky et al. |
| 2001/0044652 A1 | 11/2001 | Moore |
| 2002/0002400 A1 | 1/2002 | Drasler et al. |
| 2002/0005206 A1 | 1/2002 | Falotico et al. |
| 2002/0007209 A1 | 1/2002 | Scheerder et al. |
| 2002/0022876 A1 | 2/2002 | Richter et al. |
| 2002/0038145 A1 | 3/2002 | Jang |
| 2002/0068969 A1 | 6/2002 | Shanley et al. |
| 2002/0072511 A1 | 6/2002 | New et al. |
| 2002/0082679 A1 | 6/2002 | Sirhan et al. |
| 2002/0082680 A1 | 6/2002 | Shanley et al. |
| 2002/0094985 A1 | 7/2002 | Hermann et al. |
| 2002/0123801 A1 | 9/2002 | Pacetti et al. |
| 2002/0142039 A1 | 10/2002 | Claude |
| 2002/0155212 A1 | 10/2002 | Hossainy |
| 2003/0068355 A1 | 4/2003 | Shanley et al. |
| 2003/0199970 A1 | 10/2003 | Shanley |
| 2004/0122505 A1 | 6/2004 | Shanley |
| 2004/0127976 A1 | 7/2004 | Diaz |
| 2004/0127977 A1 | 7/2004 | Shanley |
| 2004/0144506 A1 | 7/2004 | Shanley et al. |

FOREIGN PATENT DOCUMENTS

| | | |
|---|---|---|
| EP | 0 335 341 | 10/1989 |
| EP | 0 353 341 | 2/1990 |
| EP | 0375520 | 6/1990 |
| EP | 0 470 246 | 2/1992 |
| EP | 0470 569 | 2/1992 |
| EP | 0566 245 | 10/1993 |
| EP | 0566807 | 10/1993 |
| EP | 0567 816 | 11/1993 |
| EP | 0627 226 | 12/1994 |
| EP | 0679 373 | 11/1995 |
| EP | 0734 698 | 10/1996 |
| EP | 0 747 069 | 12/1996 |
| EP | 0 770 401 | 5/1997 |
| EP | 0706 376 | 6/1997 |
| EP | 0897 700 | 2/1999 |
| EP | 0 950 386 | 10/1999 |
| EP | 1 118 325 | 7/2001 |
| EP | 1 132 058 | 9/2001 |
| EP | 1 172 074 | 1/2002 |
| EP | 1222941 | 7/2002 |
| EP | 1 223 305 | 7/2002 |
| EP | 1 236 478 | 9/2002 |
| FR | 2 764 794 | 12/1998 |
| WO | WO 90/13332 | 11/1990 |
| WO | WO 91/10424 | 7/1991 |
| WO | WO 91/12779 | 9/1991 |
| WO | WO 92/12717 | 8/1992 |
| WO | WO 92/15286 | 9/1992 |
| WO | WO 93/06792 | 4/1993 |
| WO | WO 94/21308 | 9/1994 |
| WO | WO 94/24961 | 11/1994 |
| WO | WO 95/03036 | 2/1995 |
| WO | WO 95/03795 | 2/1995 |
| WO | WO 95/24908 | 9/1995 |
| WO | WO 96/03092 | 2/1996 |
| WO | WO 96/25176 | 8/1996 |
| WO | WO 96/29028 | 9/1996 |
| WO | WO 96/32907 | 10/1996 |
| WO | WO 97/04721 | 2/1997 |
| WO | WO-9805270 | 2/1998 |
| WO | WO 98/08566 | 3/1998 |
| WO | WO 98/18407 | 5/1998 |
| WO | WO 98/19628 | 5/1998 |
| WO | WO 98/23228 | 6/1998 |
| WO | WO 98/23244 | 6/1998 |
| WO | WO 98/36784 | 8/1998 |
| WO | WO 98/58600 | 12/1998 |
| WO | WO 99/15108 | 4/1999 |
| WO | WO 99/16386 | 4/1999 |
| WO | WO 99/16477 | 4/1999 |
| WO | WO-9936002 | 7/1999 |
| WO | WO 99/44536 | 9/1999 |
| WO | WO 99/49928 | 10/1999 |
| WO | WO 99/55396 | 11/1999 |
| WO | WO 00/10613 | 3/2000 |
| WO | WO 00/45744 | 8/2000 |
| WO | WO 00/69368 | 11/2000 |
| WO | WO 00/71054 | 11/2000 |
| WO | WO 01/17577 | 3/2001 |
| WO | WO 01/45862 | 6/2001 |
| WO | WO 01/49338 | 7/2001 |
| WO | WO 91/11193 | 8/2001 |
| WO | WO 01/87376 | 11/2001 |
| WO | WO 02/17880 | 3/2002 |
| WO | WO 02/26281 | 4/2002 |
| WO | WO-04043510 | 5/2004 |
| WO | WO-04043511 | 5/2004 |

* cited by examiner

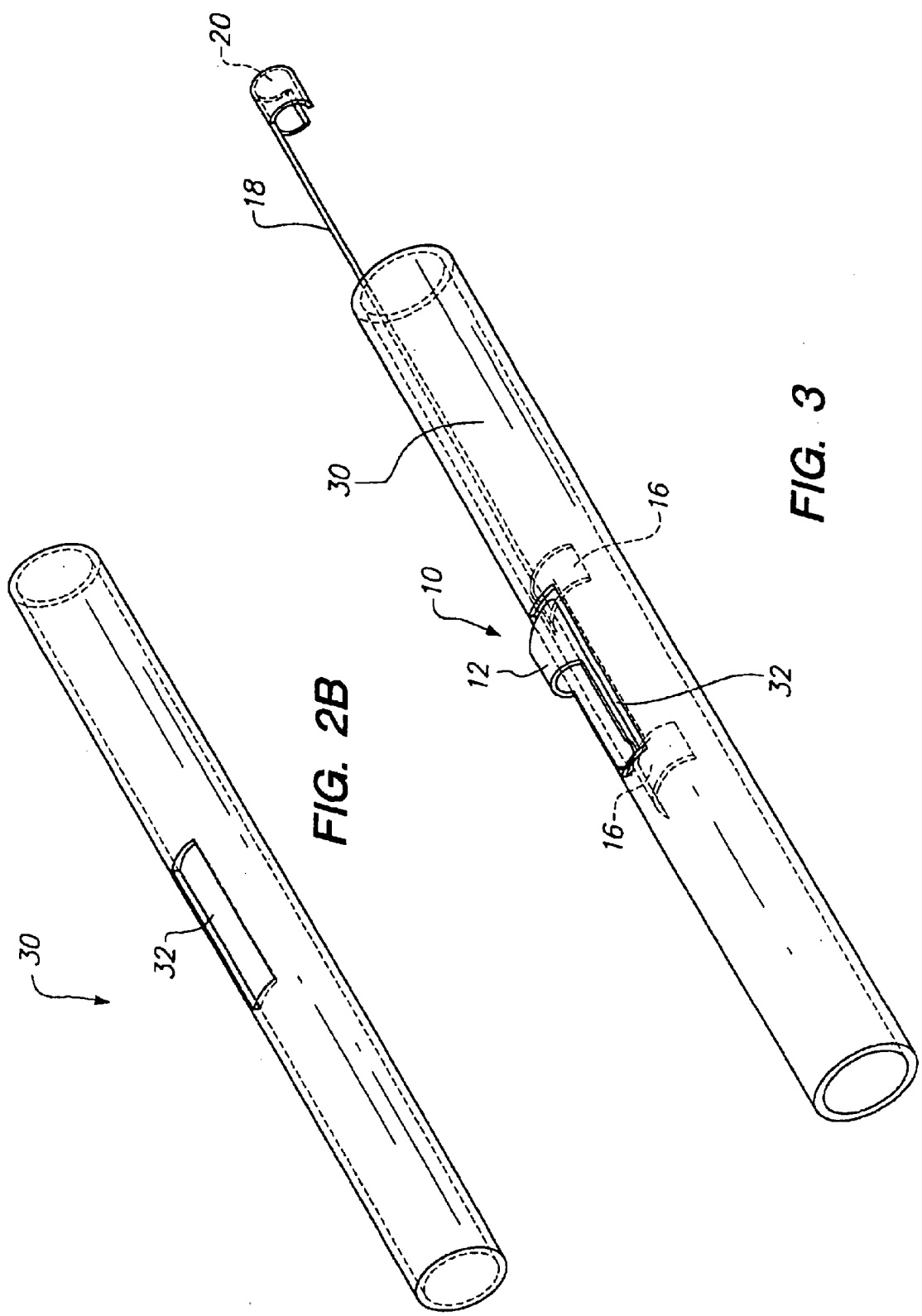

EXPANDABLE MEDICAL DEVICE DELIVERY SYSTEM AND METHOD

This is a division of application Ser. No. 09/315,885, filed May 20, 1999, now U.S. Pat. No. 6,290,673.

BACKGROUND OF THE INVENTION

1. Field of the Invention

The present invention relates to a delivery system and method for delivering tissue supporting medical devices, and more particularly to a system and method for implanting expandable, non-removable devices at the junction of two or more bodily lumens in a living animal or human to support the organs and maintain patency.

2. Summary of the Related Art

In the past, permanent or biodegradable devices have been developed for implantation within a body passageway to maintain patency of the passageway. These devices are typically introduced percutaneously, and transported transluminally until positioned at a desired location within the body passageway. The devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Frequently, the area to be supported by such devices is located at or near the junction of two or more lumens, called a bifurcation. In coronary angioplasty procedures, for example, it has been estimated that 15% to 20% of cases involve reinforcing the area at the junction of two arteries. Conventional stent implantation at such a junction results in at least partial blockage of the branch artery, affecting blood flow and impeding access to the branch artery for further angioplasty procedures.

Known techniques for treating bifurcations generally deliver a mesh tissue supporting device into the artery and position the device over the bifurcation. According to the known methods, a surgeon then attempts to create one or more branch lumen access holes by inserting a balloon through the sidewall of the mesh device, and then inflating the balloon to simply push the local features of the mesh aside. These techniques are inherently random in nature: the exact point of expansion in the device lattice cannot be predicted, and the device may or may not expand satisfactorily at that point. Tissue support provided by these known techniques for treating bifurcated arteries is similarly unpredictable. In addition, the effectiveness of such procedures is limited because many mesh devices are unable to accommodate such expansion at random locations in the device structure. Further, prior art tissue supporting device delivery systems are unable to accurately position specific device features over the branch artery opening.

Prior art tissue supporting devices for bifurcations generally have not attempted to orient the device radially at the branch lumen opening. Rather, these stents included a section along their axis or at one end at which several enlarged expansion cells were distributed uniformly around the stent circumference. The presumption was that after stent insertion, one or the other of these cells would be oriented closely enough with the branch lumen opening that the subsequent procedures mentioned above would clear the opening. One example of such a device is the Jostent® bifurcation stent design which has an 8 cell circumferential construction over half the stent length and either 2 or 3 rows of larger cells which can be post-dilated to allow access for placement in a bifurcated vessel. One problem with this technique is that the resulting density of stent features at the area of the bifurcation is so low that there is very little stent strength around the rest of the circumference of the main artery for tissue support. Thus, the lumen junction area, which requires the greatest tissue support, actually gets the lowest support. For the same reason, such tissue supporting devices also provide a low ratio of tissue coverage (metal-to-tissue area ratio) in the junction area. Low metal coverage and the resulting tissue prolapse are associated with higher restenosis rates.

Another method for deploying a stent in a bifurcating vessel is described in International Application WO98/19628. According to this method, a main stent having a substantially circular side opening and a flared stent having a flared end are used together to treat a bifurcating vessel in a two step process. In a first step, the main stent is positioned using an inflatable balloon catheter in the interior of the main stent and a stabilizing catheter extending through the side opening of the stent. The stabilizing catheter is used to place the side opening in the main stent at the opening to the branch vessel. The main stent is then expanded and the flared stent is inserted through the side opening into the vessel bifurcation. One drawback of this method is the difficulty in positioning the side opening of the main stent at a proper longitudinal and radial position at the vessel bifurcation. Another drawback of this system is the flared stent which is difficult to form and position, and may tend to protrude into the blood stream causing thrombosis.

In view of the drawbacks of the prior art bifurcated tissue supporting systems, it would be advantageous to have a delivery system capable of accurately locating a side port feature of a tissue supporting device at a branch lumen opening, in both the longitudinal and radial directions.

It would further be advantageous if the same delivery system could also be used to accurately install and orient a branch lumen second tissue supporting device.

SUMMARY OF THE INVENTION

The invention includes expandable tissue supporting devices for use at lumen junctions or bifurcations, and a delivery system and method for accurately locating, orienting, and implanting the tissue supporting devices at the lumen junction or bifurcation.

In accordance with one aspect of the present invention, a system is described for delivery of a tissue supporting device to a bifurcated body lumen. The system includes a catheter with an inflatable balloon configured to deliver an expandable tissue supporting device to the lumen, a guide member received on a side of the balloon and connected to the catheter, and a branch lumen guidewire extending along an exterior of the balloon and longitudinally slidable in the guide member.

In accordance with another aspect of the invention, a guide member is described for use in delivery of a tissue supporting device to a bifurcated body lumen in a desired longitudinal and radial position. The guide member includes a guide loop for receiving a guidewire, means for securing the guide loop to a catheter, and at least one tab extending from the guide loop for holding the guide loop in position in a side hole of a tissue supporting device to be delivered.

In accordance with a further aspect of the invention, a method of delivering a tissue supporting device to a bifurcated body lumen includes the steps of:
  providing an expandable tissue supporting device in an unexpanded configuration, the tissue supporting device having a side hole;

positioning a guide member in the side hole;

positioning a side branch guidewire in a body lumen with a distal end of the side branch guidewire extending into a side branch of a bifurcation;

delivering the tissue supporting device into the body lumen by tracking the guide member along the side branch guidewire;

positioning the tissue supporting device with the side hole aligned radially and longitudinally with an opening of the side branch; and expanding the tissue supporting device.

BRIEF DESCRIPTION OF DRAWINGS

The invention will now be described in greater detail with reference to the preferred embodiments illustrated in the accompanying drawings, in which like elements bear like reference numerals, and wherein:

FIG. 2b is a simplified, perspective view of the cylindrical tissue supporting device of FIG. 2a;

FIG. 3 is a perspective view of the guide member of FIG. 1 mounted in the side port of the tissue supporting device of FIGS. 2a and 2b;

DETAILED DESCRIPTION OF THE PREFERRED EMBODIMENTS

The invention involves a system and method for delivery of a tissue supporting device to a bifurcated artery such that, on expansion, the tissue supporting device provides side ports of a specific size and geometry to accommodate bifurcations in the artery. The delivery system is capable of accurately orienting these side ports both radially and longitudinally with respect to branch lumen openings of the artery. The delivery system achieves orientation by utilizing a guide member 10 which is positioned to extend from the side port feature of the tissue supporting device. The tissue support device is delivered to the artery on a balloon catheter which is used for expansion of the device. The guide member 10 is tracked along a side branch guidewire which extends into the branch lumen, ultimately orienting the side port of the tissue supporting device properly at the branch lumen opening. While the tissue supporting device having the side port is expanded, the guide member 10 holds the tissue supporting device in the proper position. After expansion, the guide member 10 drops out of the enlarged side port and is withdrawn with the balloon catheter assembly.

Figure 1:
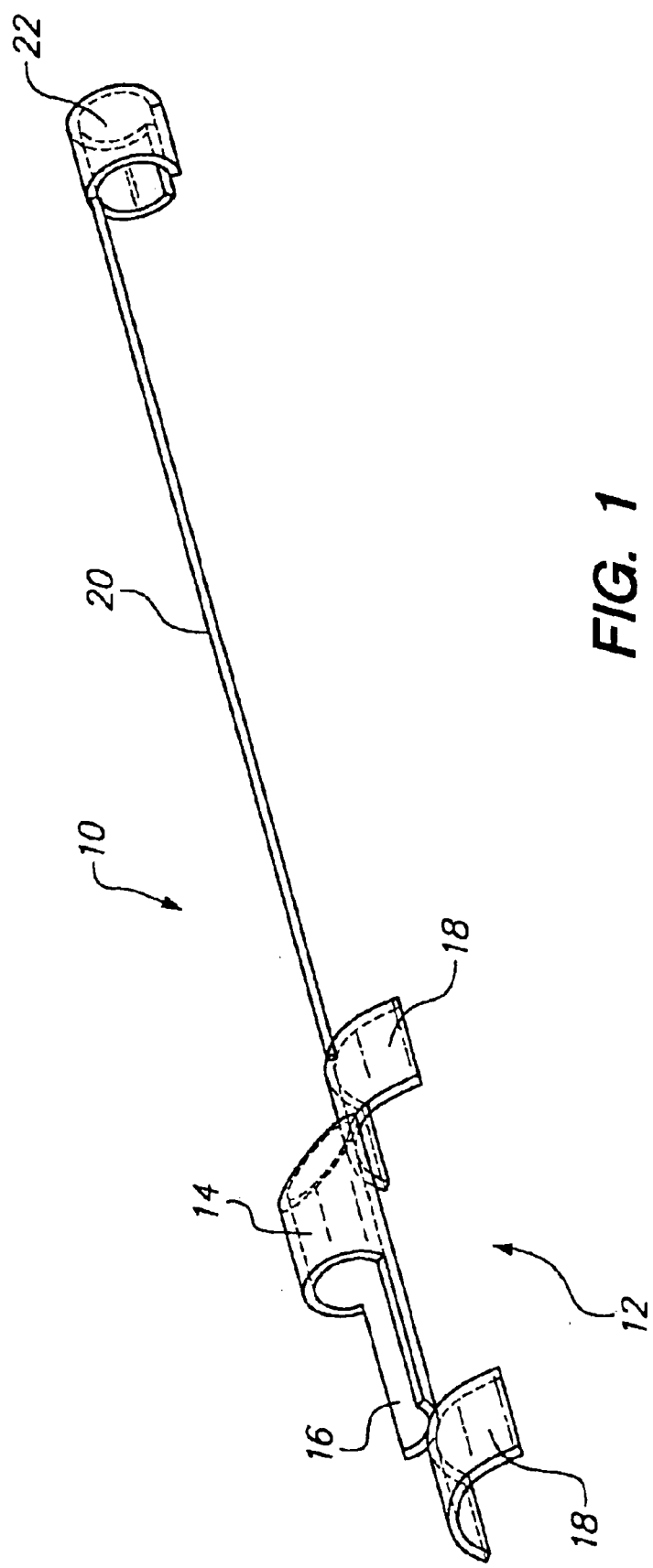
FIG. 1 is a perspective view of a guide member in accordance with the present invention.

FIG. 1 shows one embodiment of a guide member 10 in accordance with the present invention. The device 10 includes a main body 12 of which is preferably formed as a unitary piece comprising a loop 14, a spacer section 16, and two tabs 18. The inner diameter of the loop 14 is just large enough to provide clearance for a guidewire which will pass through the loop. The loop 14, spacer section 16, and tabs 18 may be integrally formed from a single piece of tubing. The radius of the tabs 18 conforms generally to the inner radius of the unexpanded tissue supporting device in which the guide loop will be mounted.

The main body 12 of the guide member 10 is attached to a crimping lug 22 via a long, flexible tether 20. The tether 20 can be a simple wire attached to the main body 12 and crimping lug 22 at either end, or can be integrally formed from the same tube as the main body 12 and the crimping lug 22.

The guide member 10 is preferably made radiopaque by one of several available methods. For example, the wall thickness of the tube may be made thick enough for good radio opacity. Alternatively, the guide loop may be made from, plated, or coated with a radiopaque material. This is not objectionable since the guide member is withdrawn immediately after the procedure and does not become a permanent implant. When the radiopaque guide member is crimped into the side port of the tissue supporting device as described in further detail below, the exact location of the side port will be clearly visible on the fluoroscope.

A preferred tissue supporting device for use in the present invention provides several capabilities not normally found in conventional stents. The tissue supporting device should provide a side port feature which will securely clamp the guide member 10 in the side port when the tissue supporting device itself is crimped to the catheter balloon. The side port should expand to some desired shape and release the guide member when the tissue supporting device is expanded. The tissue supporting device should also be capable of differential expansion; i.e. different areas of the device should expand at different balloon pressures, giving the device the ability to open in a specific sequence.

Figure 2A:
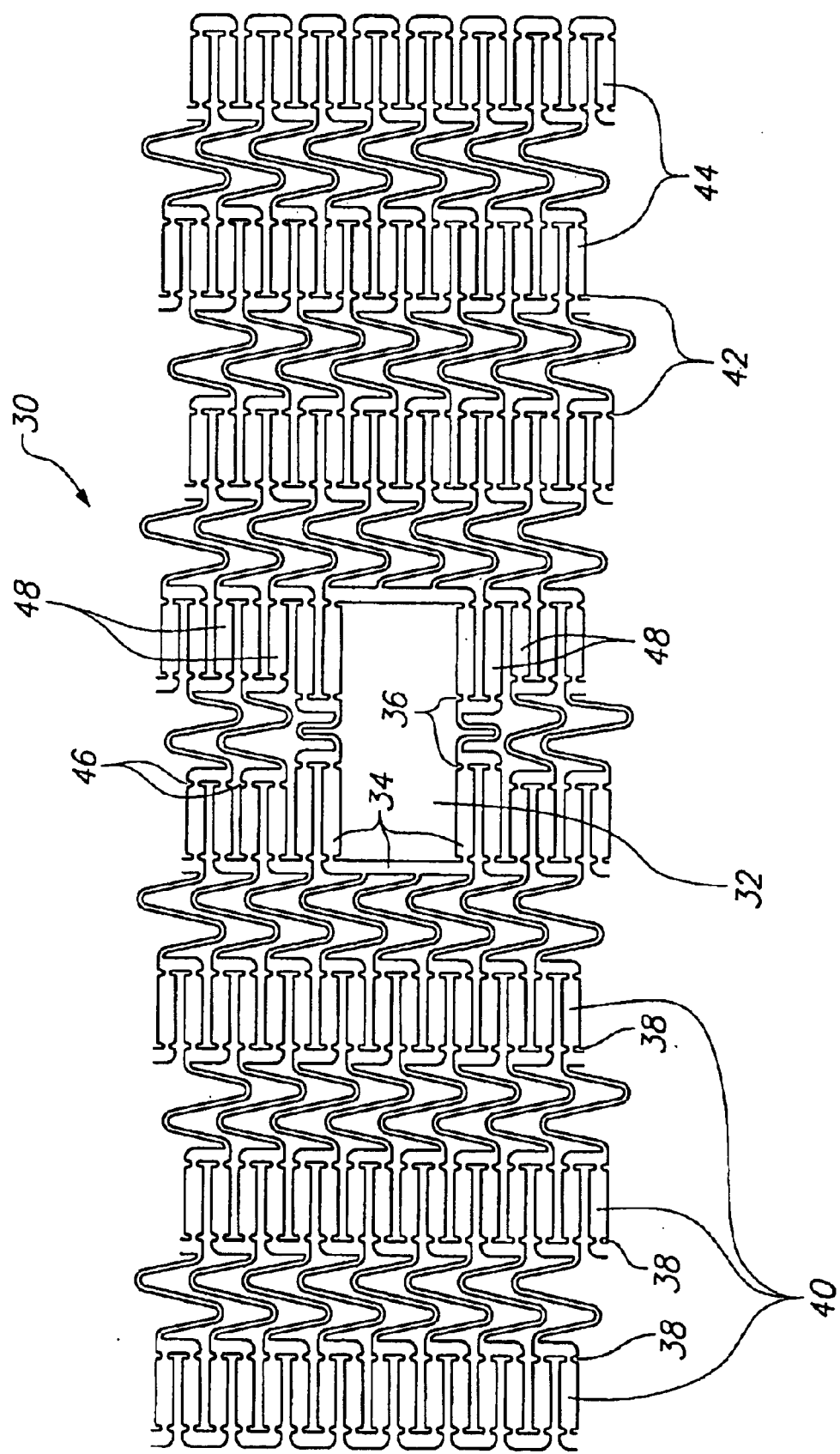
FIG. 2a is a side view of an unexpanded tissue supporting device with a side port, the device has been laid flat for ease of illustration.

FIG. 2a shows a portion of one embodiment of a cylindrical, expandable tissue supporting device 30 which has been laid flat for ease of illustration. The device 30 of FIG. 2a is shown in an unexpanded configuration and includes a rectangular side hole or port 32. FIG. 2b shows a simplified cylindrical view of the expandable tissue supporting device 30 of FIG. 2a, with the side port feature 32 shown as a rectangular hole in one side. This embodiment of the tissue supporting device 30 relies on the use of ductile hinges which interconnect a plurality of struts to achieve the desired performance features. Tissue supporting devices of the type shown in FIG. 2a are described in further detail in U.S. patent application Ser. No. 09/183,555, filed Oct. 29, 1998, and in U.S. patent application Ser. No. 09/315,892, filed on even date herewith which are both incorporated herein by reference in their entirety.

As shown in FIGS. 2a and 2b, the side hole 32 initially takes the form of a rectangular hole in the unexpanded tissue supporting device 30. The side hole 32 is bordered by six struts 34 that are in turn linked by ductile hinges 36. The rectangular side hole 32 fits the profile of the guide loop feature 10 closely, and the excellent crimping properties of the ductile hinges allow the hole to close tightly around the guide loop feature when the tissue supporting device 30 is crimped onto the catheter balloon. When the tissue supporting device 30 is expanded, such as by inflation of a balloon, the side hole feature 32 will expand to form an octagonal hole, releasing the guide member 10.

In the tissue supporting device 30 of FIG. 2a, the ductile hinges 38 linking struts 40 on the left or proximal end of the device are wider than the ductile hinges 42 linking struts 44 on the right or distal end of the device. The width of the ductile hinges is measured in the circumferential direction of the device 30. As balloon pressure is increased during expansion of the device 30 the distal end of the device will open before the proximal end due to the different configuration of the ductile hinges at the two ends of the device. The tissue supporting device 30 should be selected so that the device is capable of expansion beyond a nominal expansion which corresponds to an interior diameter of the lumen to be supported. This will ensure that the tissue supporting device 30 can be expanded to the desired diameter of the expanded lumen allowing for variations in artery diameters. Allowing for some additional expansion beyond the nominal expansion of the tissue support device 30 means that some of the struts around the circumference of the device will not reach their locking angle when the device has been installed. Accordingly, if the struts 48 all open to their full extent before the struts 34 that border the side hole 32, this may result in the side hole not being fully opened when the tissue supporting device is installed. The partially opened side hole may partially block access to the branch artery. Accordingly, the ductile hinges 36 connecting the struts 34 that border the side hole 32 are preferably somewhat narrower than the ductile hinges 46 of the surrounding struts 48. This will guarantee that the hole feature opens to its final shape before the surrounding struts 48 reach full expansion.

The present invention will be described with respect to a tissue supporting device having ductile hinges such as the device illustrated in FIG. 2a. However, it should be understood that the system and method according to the present invention may also be used for delivery of other known tissue supporting devices having side holes.

FIG. 3 illustrates the guide member 10 inserted in the tissue supporting device 30 such that the loop 14 projects out through the rectangular side hole 32 and is retained in the hole. The guide member 10 is retained in the side hole 32 by the tabs 16 which are trapped between the tissue supporting device 30 and a balloon catheter assembly.

Figure 4:
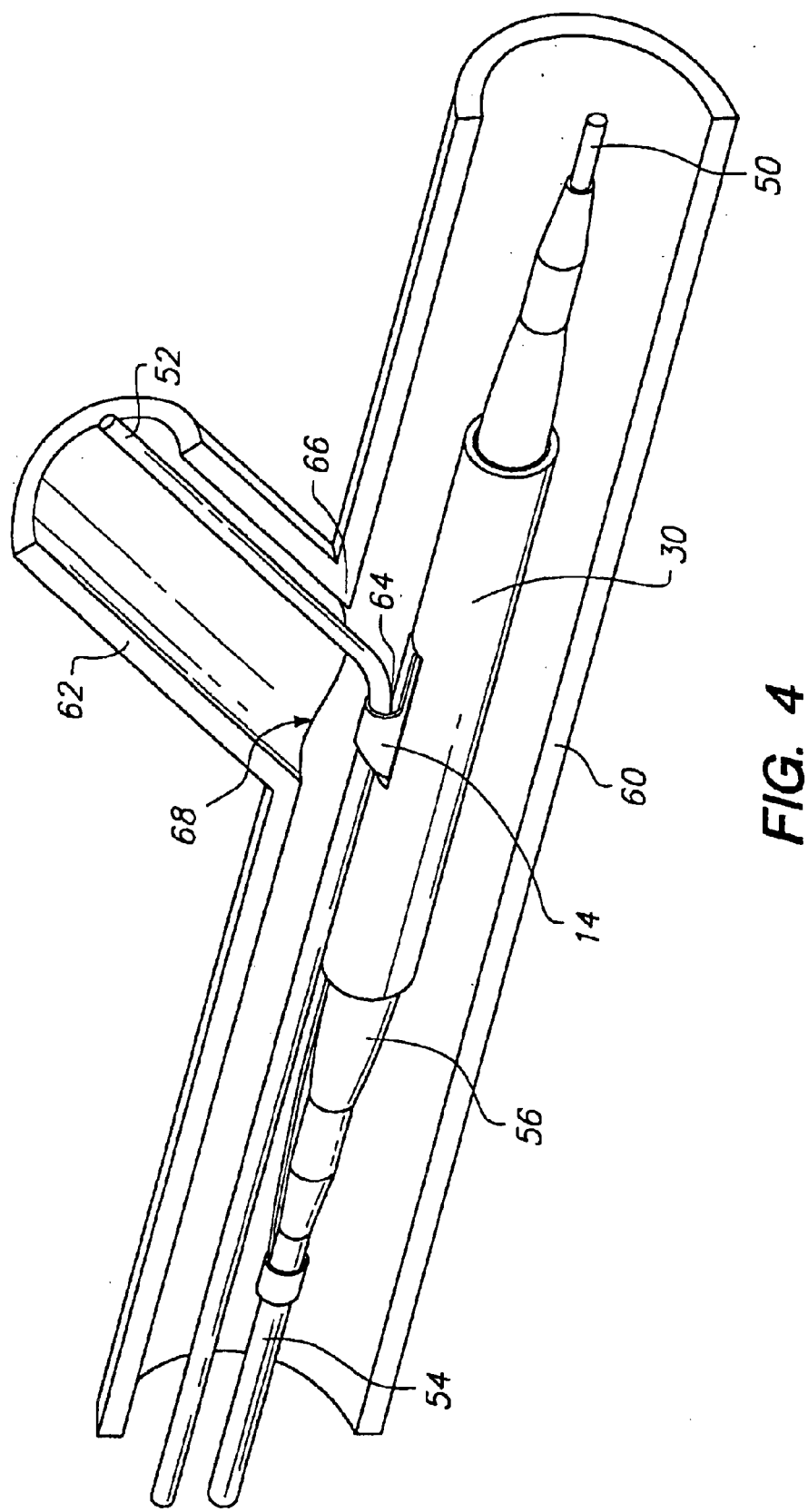
FIG. 4 is a perspective view of the tissue supporting device of FIGS. 2a and 2b as it is inserted to a junction of two arteries with a balloon catheter and two guidewires.

As shown in FIG. 4, the tissue supporting device 30 and guide member 10 are mounted on a catheter balloon 56 and the tissue supporting device 30 is crimped down onto the balloon in a known manner. The crimping process causes the strut elements 34 of the rectangular side hole 32 in the tissue supporting device 30 to close around the guide loop 10, locking the guide loop into place in the side hole. The crimping lug 22 of the guide loop 10 is crimped around the catheter 54 just below the proximal end of the balloon assembly, securing the guide member 10 to the catheter. The catheter and tissue supporting device assembly is now ready for insertion and deployment.

The guide member 10 may take on other configurations as long as the guide member forms a short tube or loop positioned on or secured to the balloon/catheter assembly in such a way that it passes out through the side hole of the tissue supporting device when the device is crimped or otherwise secured on the balloon 56. For example, the guide member may be formed from a plastic tube and secured directly to the balloon, such as, by an adhesive.

Prior to insertion of the catheter and tissue supporting device assembly, two catheter guidewires are installed by the operator. A first guidewire 50 follows the main artery 60 as shown in FIG. 4, and a second guidewire 52 is inserted into the branch artery 62. The catheter 54 having the tissue supporting device 30 mounted on the balloon 56 at the distal end of the catheter is tracked over the main artery guidewire 50. The branch artery guidewire 52 is threaded through the guide loop 12 that projects through the top of the tissue supporting device 30. The assembly is then fed through a catheter guide tube (not shown) to the site of the bifurcation 68. As the catheter assembly approaches the bifurcation 68, the clevis 64 formed by the tissue supporting device 30 and the branch artery guidewire 52 comes to rest against the distal side 66 of the branch artery opening. The guide loop 14, and thus the side port 32 of the tissue supporting device 30 in which it is crimped, is now located directly under the branch artery opening, and the device is ready for deployment. The spacer 16 spaces the guide loop a predetermined distance from the distal edge of the side hole 32 so that the side hole will be properly aligned with the opening of the bifurcation 68.

Figure 5:
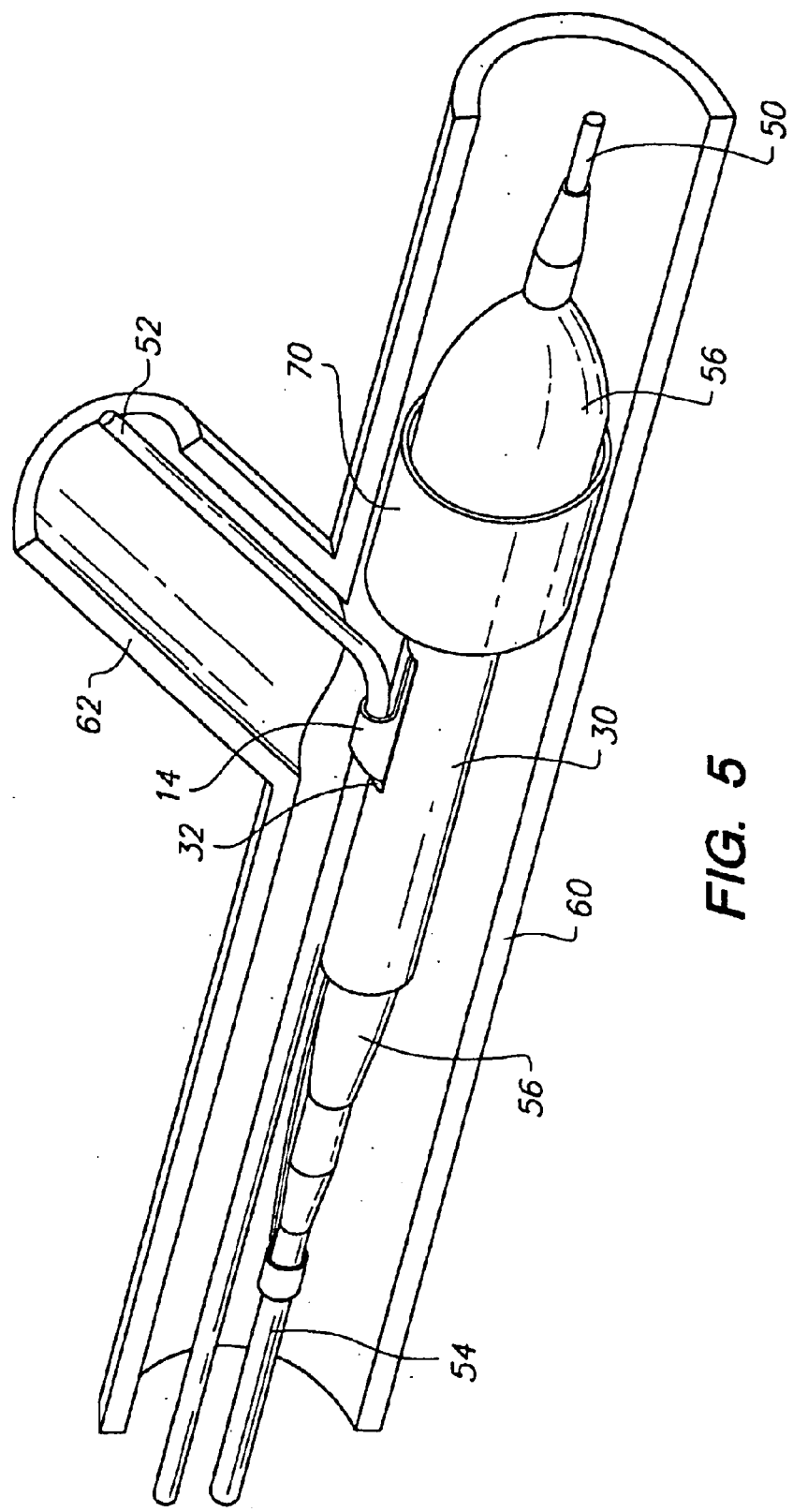
FIG. 5 is a perspective view illustrating a first step of the implantation sequence: expansion of the distal end of the tissue supporting device.

To deploy the tissue supporting device 30, pressure is increased in the catheter balloon 56 until the distal end 70 of the tissue supporting device expands to the lumen diameter of the main artery 60. This procedure locks the tissue supporting device 30 in place in the desired radial and longitudinal orientation as shown in FIG. 5.

Figure 6:
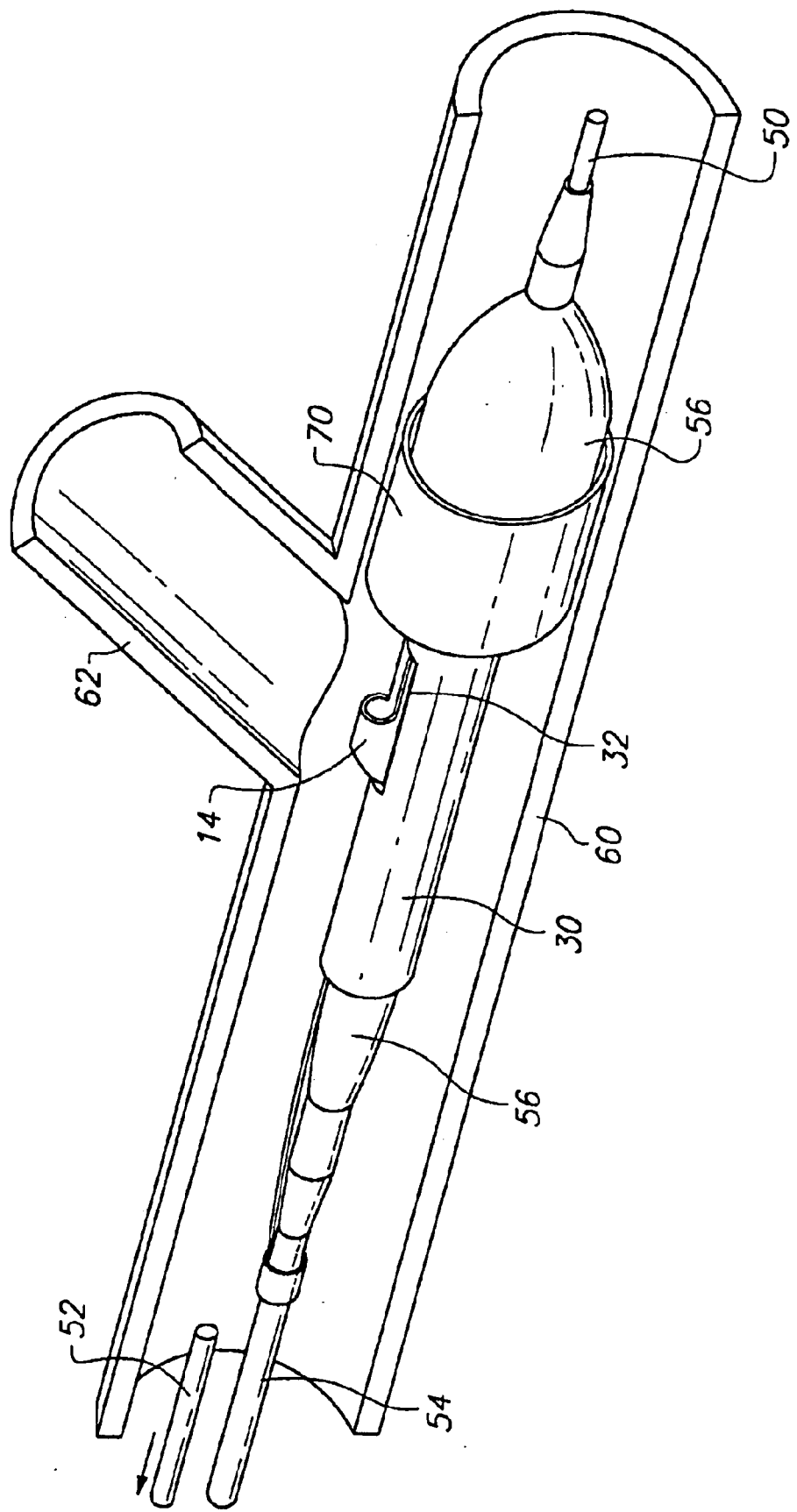
FIG. 6 is a perspective view illustrating a second step of the implantation sequence: withdrawal of the branch lumen guidewire.

Next, the side branch guidewire 52 is withdrawn from the branch lumen 62 and the guide loop 14, and retracted to a position slightly behind the proximal end of the catheter balloon 56 as shown in FIG. 6. The side branch guidewire 52 is free to move back and forth longitudinally because the proximal end of the tissue supporting device 30 has not been expanded. It is desirable to withdraw the side branch guidewire 52 temporarily while completing expansion of the proximal end of the tissue supporting device 30 to avoid pinning the side branch guidewire between the expanded tissue supporting device 30 and the lumen wall. This is the reason that differential expansion capability is beneficial in the tissue supporting device 30.

Figure 7:
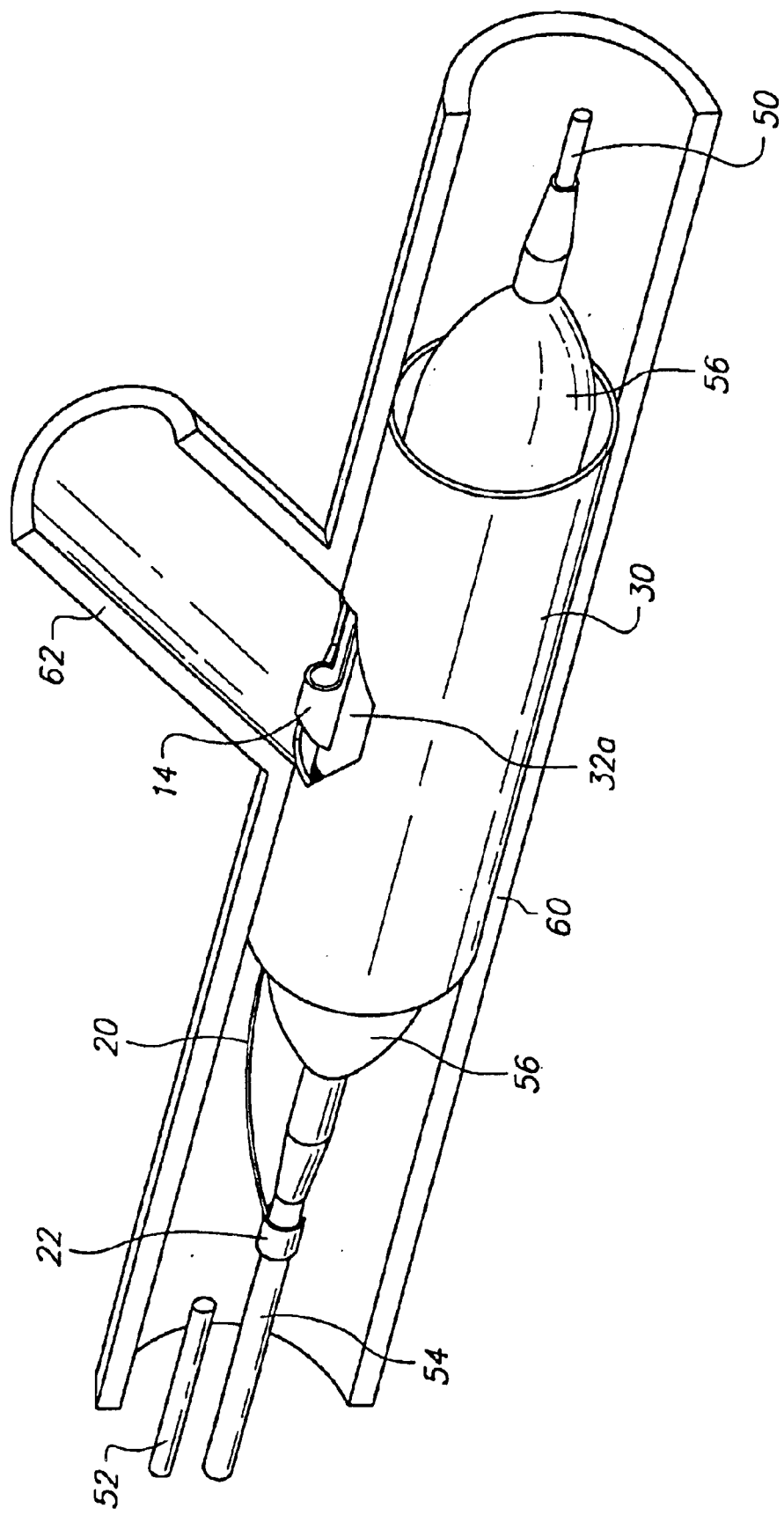
FIG. 7 is a perspective view illustrating a third step of the implantation sequence: expansion of the side port area and proximal end of the tissue supporting device.

After withdrawal of the side branch guidewire 52, pressure in the catheter balloon 56 is increased further, until the side port area and the proximal end of the tissue supporting device 30 expand to their full extent. During expansion of the side port area, the spacer 16 and loop 14 maintain the longitudinal dimension of the side hole 32 and prevent longitudinal contraction of the side hole during expansion. The main artery tissue supporting device 30 is now fully deployed with a fully open side port 32a of specific geometry positioned over the branch lumen opening, and a full complement of strut elements deployed around the remainder of the artery opposite the side port to provide good tissue support as shown in FIG. 7.

Figure 8:
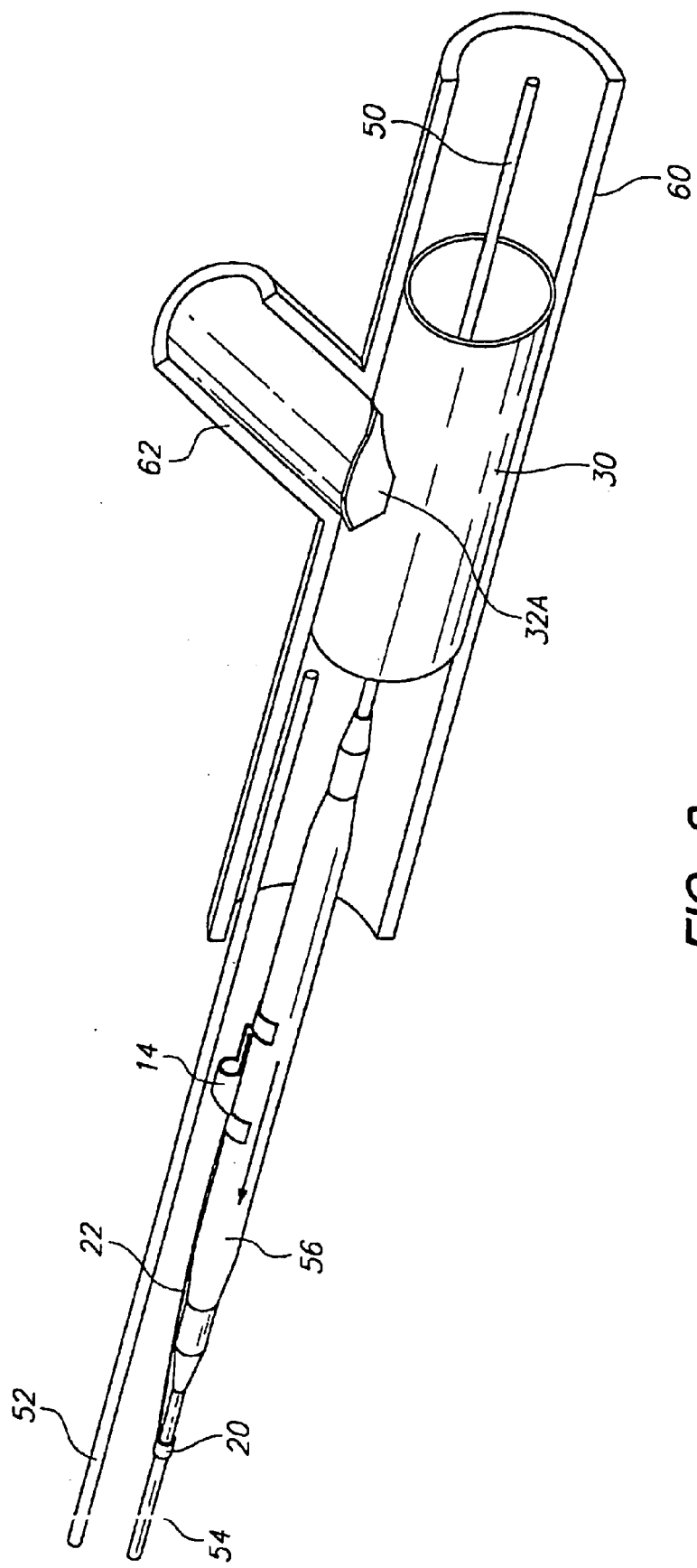
FIG. 8 is a perspective view illustrating a fourth step of the implantation sequence: deflation and withdrawal of the balloon and guide loop.

The catheter balloon 56 is then deflated, allowing the guide member 10 to drop out of the enlarged side port 32a. The deflated catheter/balloon assembly is then withdrawn, pulling the guide member 10 along with it via the tether 18 and crimping lug 22 as shown in FIG. 8. After the catheter/balloon/guide loop assembly has been withdrawn, the side branch guidewire 52 may be reinserted through the tissue supporting device enlarged side hole 32a and into the branch lumen 62 for subsequent procedures.

Figure 9:
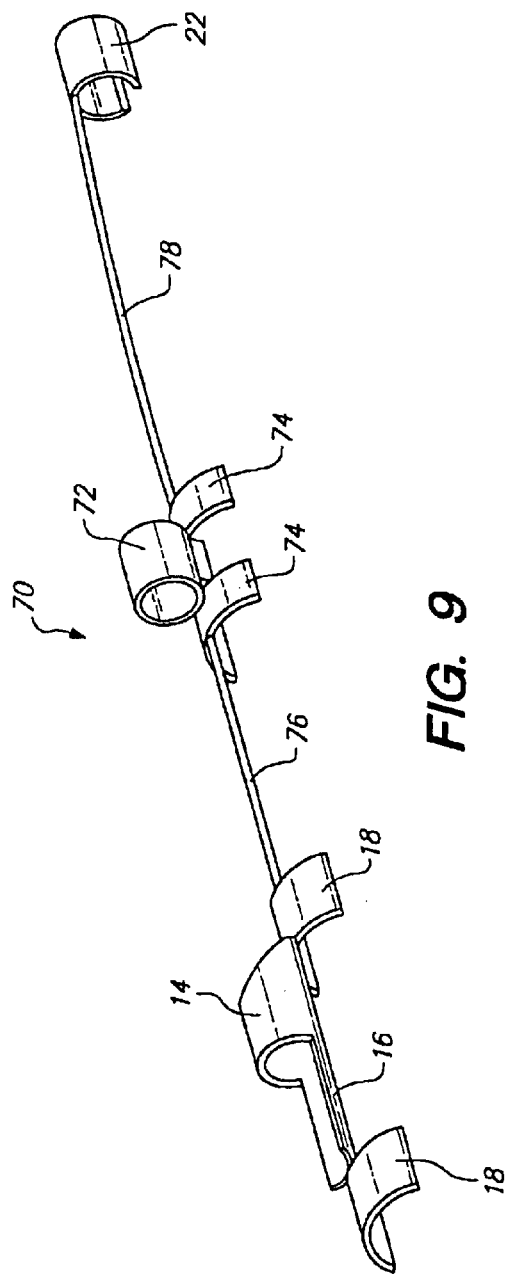
FIG. 9 is a perspective view of a guide member with an auxiliary guide loop in accordance with the present invention.
Figure 10:
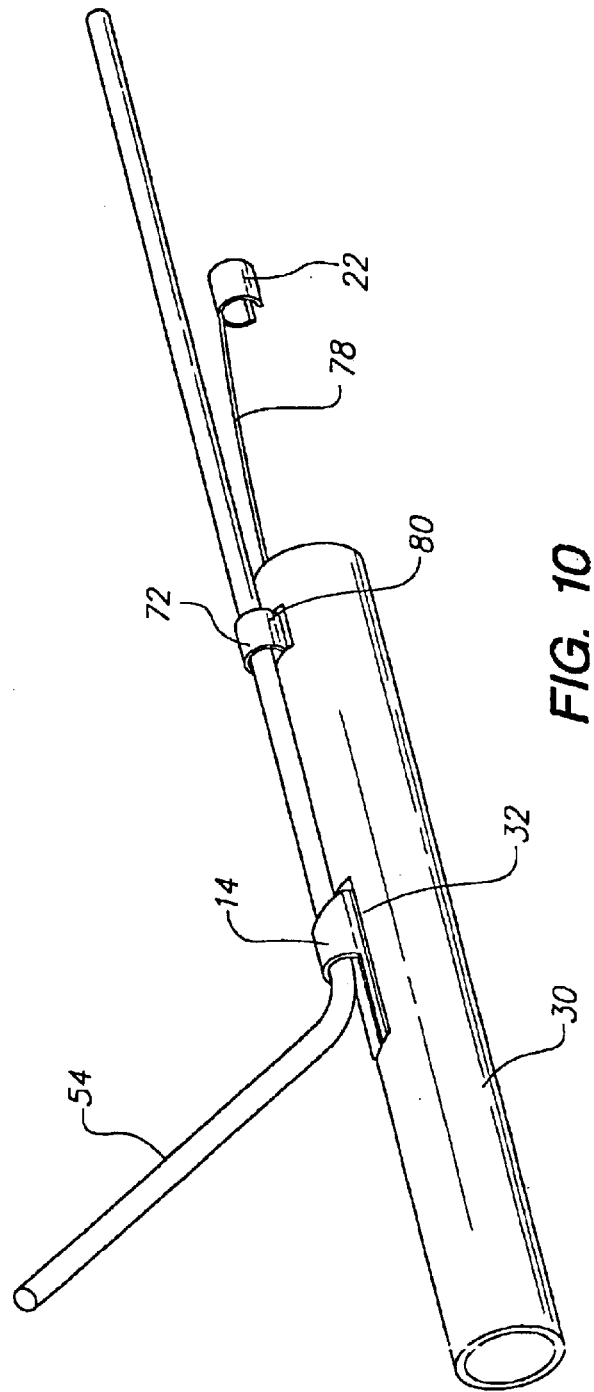
FIG. 10 is a perspective view of the guide member of FIG. 9 mounted in a tissue supporting device having two side ports.

The orientation accuracy of the delivery system can be improved by the addition of one or more auxiliary guide loops to the guide member as illustrated in FIGS. 9 and 10. The guide member 70 as shown in FIG. 9 includes the main loop 14 with the spacer section 16 and tabs 18, and an auxiliary loop 72. The auxiliary loop 72 is also provided with tabs 74 which conform generally to the inner radius of the unexpanded tissue supporting device in which the guide loop will be mounted. The auxiliary loop 72 is connected the main loop 14 by a first tether 76 and is connected to the crimping lug 22 by a second tether 78. As shown in FIG. 10, the auxiliary loop 72 extends through a second side port feature 80 in the tissue supporting device 30. The additional one or more auxiliary loops 72 are located proximal to the primary guide loop 14. The installation procedure for the tissue supporting device 30 using the guide member 70 shown in FIGS. 9 and 10 would be performed in the same manner as discussed above with respect to the embodiment employing a single guide loop, however, the side branch guidewire 52 extends through both the main guide loop 14 and the auxiliary loop 72.

One common procedure to follow implantation of the tissue supporting device 30 into the main lumen would be implantation of a second tissue supporting device in the branch lumen 62. A procedure very similar to the one just outlined could be used to accomplish this task, by simply reversing the roles of the main lumen and branch lumen guidewires. As above, a guide member is inserted into the side port of a second tissue supporting device, and the assembly is crimped down on a conventional catheter balloon. In this case, the catheter and tissue supporting device assembly is mounted on the side branch guidewire 52, and the main artery guidewire 50 is threaded through the guide member. As before, the entire assembly is fed to the bifurcation site, where the clevis formed by the tissue supporting device and main artery guidewire 50 comes to rest against the distal side of the branch lumen opening. In this case, the side-port border-struts of the previously implanted tissue supporting device 30 are also in place to provide an even more accurate stop for aligning the side hole edge of the incoming tissue supporting device at the distal side of the bifurcation.

The tissue supporting device deployment sequence for deploying the second device would now proceed as before: the distal end of the branch tissue supporting device would be expanded in the branch artery, anchoring the tissue supporting device in position, and the main artery guidewire 50 would be retracted below the proximal end of the catheter balloon. The unexpanded proximal end of the second tissue supporting device now extends back into the main artery, with the tissue supporting device side port facing downstream in the main artery.

When expansion of the second tissue supporting device is completed, the proximal end of the second tissue supporting device will be implanted in the main artery, with the second tissue supporting device bent around the proximal side of the branch artery orifice. The side port of the second tissue supporting device will open exactly opposite this bend, since the leading edge of the side port was initially located at the bifurcation junction as described above. The side port thus opens to permit flow through the main artery, and the tissue supporting device struts arrayed opposite the side port provide support to the proximal side of the branch artery orifice (the bend area). After implantation has been completed, the catheter/balloon/guide loop assembly is withdrawn, completing the procedure.

Although the invention has been described with respect to providing support for bifurcated lumens in arteries, it should be understood that the invention may also be used to provide support for bifurcations in other bodily lumens.

While the invention has been described in detail with reference to the preferred embodiments thereof, it will be apparent to one skilled in the art that various changes and modifications can be made and equivalents employed, without departing from the present invention.

What is claimed is:

1. A guide member for use in delivery of a tissue supporting device to a bifurcated body lumen in a desired longitudinal and radial position, the guide member comprising:
    a guide loop for receiving a guidewire;
    means for securing the guide loop to a catheter; and
    at least one tab extending from the guide loop for holding the guide loop in position in a side hole of a tissue supporting device to be delivered.

2. The guide member of claim 1, wherein the at least one tab is a curved member having a radius of curvature which corresponds substantially to an inner radius of the tissue supporting device to be delivered.

3. The guide member of claim 1, wherein the guide loop and at least one tab are formed from a single piece of tubing.

4. The guide member of claim 1, wherein the means for securing the guide loop to a catheter includes a crimping lug which is connected to the guide loop by a tether.

5. The guide member of claim 1, further comprising a spacer member connected to the guide loop and configured to space the guide loop a predetermined distance from a distal edge of the side hole of the tissue supporting device when the guide loop is positioned in the side hole of the tissue supporting device.

6. The guide member of claim 1, further comprising an auxiliary guide loop positioned proximally of the guide loop.

7. A system for delivery of a tissue supporting device to a bifurcated body lumen, the system comprising:
    a catheter with an inflatable balloon, the inflatable balloon configured to deliver an expandable tissue supporting device to the lumen;
    a guide member received on a side of the balloon and connected to the catheter by a connection restricting axial movement between the guide member and the catheter; and
    a branch lumen guidewire extending along an exterior of the balloon and longitudinally slidable in the guide member.

8. The system of claim 7, wherein the guide member extends radially from the side of the balloon and is arranged to be received in a side hole of a tissue supporting device mounted on the balloon.

9. The system of claim 7, wherein the guide member includes a guide loop.

10. The system of claim 7, wherein the guide member includes a fastener connected to the catheter.

11. The system of claim 7, wherein the guide member includes first and second guide loops which are arranged to be received in side holes of a tissue supporting device mounted on the balloon.

12. A system for delivery of a tissue supporting device to a bifurcated body lumen, the system comprising:
    a catheter with an inflatable balloon, the inflatable balloon configured to deliver an expandable tissue supporting device to the lumen;

a guide member received on a side of the balloon and connected to the catheter by a fastener; and a guidewire extending along an exterior of the balloon and longituninally slidable in the guide member.

13. The system of claim 12, wherein the guide member extends radially from the side of the balloon and is arranged to be received in a side hole of a tissue supporting device mounted on the balloon.

14. The system of claim 12, wherein the guide member includes a guide loop.

* * * * *